(12) United States Patent
DePaul

(10) Patent No.: US 9,204,834 B1
(45) Date of Patent: Dec. 8, 2015

(54) GLUCOSE BLOOD MONITOR

(71) Applicant: Patricia A. DePaul, Portland, OR (US)

(72) Inventor: Patricia A. DePaul, Portland, OR (US)

( * ) Notice: Subject to any disclaimer, the term of this patent is extended or adjusted under 35 U.S.C. 154(b) by 416 days.

(21) Appl. No.: 13/716,755

(22) Filed: Dec. 17, 2012

(51) Int. Cl.
| | | |
|---|---|---|
| A61B 5/157 | (2006.01) | |
| A61B 5/15 | (2006.01) | |
| A61B 5/145 | (2006.01) | |
| A61B 5/151 | (2006.01) | |

(52) U.S. Cl.
CPC ............... *A61B 5/157* (2013.01); *A61B 5/1411* (2013.01); *A61B 5/14532* (2013.01); *A61B 5/15113* (2013.01); *A61B 5/15117* (2013.01); *A61B 5/15174* (2013.01); *A61B 5/15178* (2013.01); *A61B 5/150389* (2013.01)

(58) Field of Classification Search
CPC ........... A61B 5/14532; A61B 5/15184; A61B 5/15146; A61B 5/15117; A61B 5/15113; A61B 5/15196; A61B 5/15153; A61B 5/15178; A61M 2005/004
See application file for complete search history.

(56) References Cited

U.S. PATENT DOCUMENTS

| | | |
|---|---|---|
| 5,786,584 A | 7/1998 | Button et al. |
| D439,334 S | 3/2001 | Hershberger et al. |
| 6,530,892 B1 | 3/2003 | Kelly |
| 2003/0191415 A1 * | 10/2003 | Moerman et al. ............. 600/584 |
| 2005/0240119 A1 | 10/2005 | Draudt et al. |

* cited by examiner

*Primary Examiner* — Paul Hyun
(74) *Attorney, Agent, or Firm* — Crossley Patent Law

(57) ABSTRACT

A glucose blood monitor that includes a cartridge releasably insertable into an interior cavity of a housing, said cartridge including a plurality of lancet strips vertically disposed therein, each of said plurality of lancet strips including a hollow needle and a test strip, wherein each of said plurality of lancet strips is cycled from a first cavity within the cartridge, to a prime position for use, to a read position for analysis of a collected blood sample, then to a used position within a second cavity in the cartridge, whereby used needles and test strips are interiorly retained within the cartridge for safe disposal of the cartridge as a whole subsequent use of the last of the plurality of lancet strips.

13 Claims, 5 Drawing Sheets

GLUCOSE BLOOD MONITOR

BACKGROUND OF THE INVENTION

Various types of glucose blood monitoring devices are known in the prior art. However, what is needed is a glucose blood monitor that includes a cartridge releasably insertable into an interior cavity of a housing, said cartridge including a plurality of lancet strips vertically disposed therein, each of said plurality of lancet strips including a hollow needle and a test strip, wherein each of said plurality of lancet strips is cycled from a first cavity within the cartridge, to a prime position for use, to a read position for analysis of a collected blood sample, thence to a used position within a second cavity in the cartridge, whereby used needles and test strips are interiorly retained within the cartridge for safe disposal of the cartridge as a whole subsequent use of the last of the plurality of lancet strips.

FIELD OF THE INVENTION

The present invention relates to a glucose blood monitor and more particularly, to a Glucose blood monitor that includes a cartridge releasably insertable into an interior cavity of a housing, said cartridge including a plurality of lancet strips vertically disposed therein, each of said plurality of lancet strips including a hollow needle and a test strip, wherein each of said plurality of lancet strips is cycled from a first cavity within the cartridge, to a prime position for use, to a read position for analysis of a collected blood sample, thence to a used position within a second cavity in the cartridge, whereby used needles and test strips are interiorly retained within the cartridge for safe disposal of the cartridge as a whole subsequent use of the last of the plurality of lancet strips.

SUMMARY OF THE INVENTION

The general purpose of the glucose blood monitor, described subsequently in greater detail, is to provide a glucose blood monitor which has many novel features that result in a glucose blood monitor which is not anticipated, rendered obvious, suggested, or even implied by prior art, either alone or in combination thereof.

In the modern age, due to poor diet and exposure to processed foods, rates of diabetes infection have skyrocketed. Many individuals are required to regularly monitor their blood sugar levels to manually adjust their insulin levels accordingly and maintain blood sugar levels between acceptable norms. Many devices for measuring blood glucose levels are on the market today. Many of them require the loading of a test strip into a meter manually. Typically, a user pricks his or her finger, places a drop of blood on the test strip, and then manually loads the test strip into the device whereupon a reading is communicated. The test strip must then be disposed of. This creates a potential biohazard—even in small quantities, blood may contain pathogens infectious to those who come into contact with it.

Devices also exist on the market where blood is dripped directly onto a reader, without the use of a test strip to hygroscopically retain the blood. These devices must be repeatedly cleaned, or the test area discarded. A similar biohazard results.

What is needed is a glucose blood monitor that includes a cartridge releasably insertable into an interior cavity of a housing, said cartridge including a plurality of lancet strips vertically disposed therein, each of said plurality of lancet strips including a hollow needle and a test strip, wherein each of said plurality of lancet strips is cycled from a first cavity within the cartridge, to a prime position for use, to a read position for analysis of a collected blood sample, and thence to a used position within a second cavity in the cartridge, whereby used needles and test strips are interiorly retained within the cartridge for safe disposal of the cartridge as a whole.

Wherefore, the present glucose blood monitor has been devised to enable single handed use for continuous monitoring of blood glucose levels. The device includes a cartridge releasably insertable into an interior cavity within a housing, the cartridge having a plurality of lancet strips therein, each of which lancet strips include a hollow needle and a test strip. Use of the device cycles each of the plurality of lancet strips from a first cavity in the cartridge, to a prime position for firing, to a read position subsequent firing, and thence to a used position when a subsequent lancet strip is loaded into the prime position.

Each of the plurality of lancet strips is thus cycled from the first cavity into a second cavity within the cartridge, each of the plurality of lancet strips occupying the used position in the second cavity after use.

The instant glucose blood monitor includes a housing having a front side, a bottom side, a top side, and a rear side. The interior cavity is accessible through the bottom side. A muzzle opening is disposed upon the front side proximal to the top side, said muzzle opening configured to enable the hollow needle of one of the plurality of lancet strips to protrude therethrough when said lancet strip is fired.

A meter display assembly is slidably disposed atop the device within a slot. The meter display assembly is moveable form an unfired position proximal an occipital bulb disposed upon the rear side proximal the top side, and a fired position proximal the front side. An elastic band is disposed around the occipital bulb and attached the meter display assembly. The elastic band returns the meter display assembly to the unfired position subsequent firing of the device.

A trigger mechanism is disposed upon the rear side underneath the occipital bulb. The trigger mechanism is pivotally disposed within the rear side by means of a swivel pin. The trigger mechanism is thus moveable between a depressed position and a non-depressed position. The trigger mechanism is configured to be depressed by the thenar of a user's hand when the device is grasped. Deployment of the trigger into the depressed position releasably engages a hammer mechanism by which the device is fired, and a lancet strip is forcibly engaged so that the hollow needle is projected through the muzzle opening. A first spring member in operational communication with the trigger mechanism returns the trigger mechanism into the non-depressed position.

To cock the device for use, a cocking pin is disposed protruding through the front side proximal the muzzle opening. The cocking pin engages with the hammer mechanism inside the housing when depressed. It is envisioned that the act of placing the device against the epidermis of a user will concurrently cock the device. The cocking pin thus engages with a rounded hammer member of the hammer mechanism, and pushes said hammer mechanism into a first position against the action of a coiled second spring member. Simultaneously, one of the plurality of lancet strips is moved to the prime position. The device is now cocked. When the trigger mechanism is depressed, the hammer mechanism is released and the coiled second spring member forcibly contracts whereby the hammer mechanism engages with a foot member disposed upon the meter display assembly, and the meter display assembly is accelerated towards the muzzle opening forcibly engaging said lancet strip in the process.

An elastic coil is disposed within the cartridge, said elastic coil wound around each of the plurality of lancet strips. When one of the plurality of lancet strips is fired, the elastic coil forcibly retracts the hollow needle from the muzzle opening to return the lancet strip to the prime position. When the device is then cocked a subsequent time, said lancet strip is moved to the used position and a subsequent lancet strip is elevated to the prime position.

Blood drawn by the hollow needle is hygroscopically retained onto the test strip. The movement of the meter display assembly engages the test strip into the meter display assembly wherein the blood sample is analyzed and a blood glucose level is displayed on a digital readout disposed atop the meter display assembly.

A battery compartment is disposed within the interior cavity and wired in circuit with the meter display assembly. A button cell is disposed exteriorly upon the cartridge. When the cartridge is inserted into the interior cavity, the button cell is automatically engaged with the battery compartment to power the meter display assembly. Thus, the button cell is replaceable with each cartridge, as desired.

Each of the plurality of lancet strips moves from the first cavity to the second cavity within the cartridge, cycling therethrough with each use of the device. A lancet strip, then, is moved from the top of the first cavity and raised to the prime position when the device is cocked. When the device is fired, the hollow needle is forced through the muzzle opening by means of the hammer mechanism acceleratively engaging the meter display assembly. The hollow needle is retracted back to the prime position by means of the elastic coil disposed within the cartridge encircling each of the plurality of lancet strips. Concurrently, the test strip is engaged with the meter display assembly and a reading is actuated. Subsequent cocking of the device thereafter moves the lancet strip to the used position in the second cavity, and a second lancet strip is raised to the prime position. Thusly, one by one, each of the plurality of lancet strips is moved upwardly from the first cavity downwardly into the second cavity with each firing of the device.

Because the cartridge is preloaded with lancet strips, a user merely loads the device with a cartridge for use. Because the cartridge retains the used lancet strips in the second cavity, which is removed from the first cavity by means of an interior wall, there is no disposal of each test strip required. The cartridge is merely discarded when each of the plurality of lancet strips has been used. Because the used test strips and needles are retained in the second cavity within the cartridge, the cartridge may be safely disposed of without potential biohazard.

The absence of a lancet strip in the prime position is communicated to the user by means of the digital readout, whereby a user is alerted to the expired status of the cartridge. The cartridge is then ejected and a subsequent cartridge is loaded into the device.

Thus has been broadly outlined the more important features of the present glucose blood monitor so that the detailed description thereof that follows may be better understood and in order that the present contribution to the art may be better appreciated.

Objects of the present glucose blood monitor, along with various novel features that characterize the invention are particularly pointed out in the claims forming a part of this disclosure. For better understanding of the glucose blood monitor, its operating advantages and specific objects attained by its uses, refer to the accompanying drawings and description.

BRIEF DESCRIPTION OF THE DRAWINGS

Figures

DETAILED DESCRIPTION OF THE DRAWINGS

Figure 1:
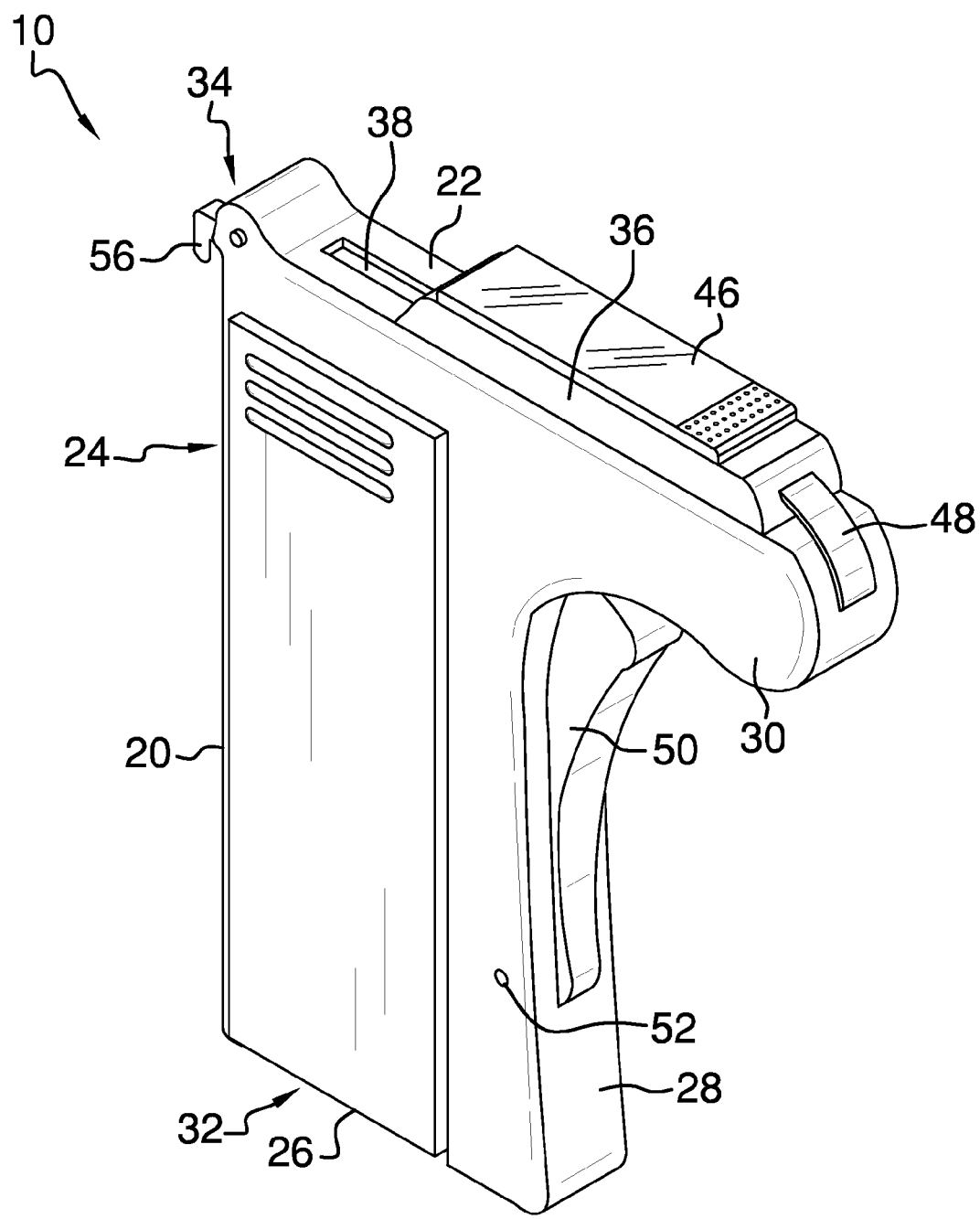
FIG. 1 is an isometric view.
Figure 2:
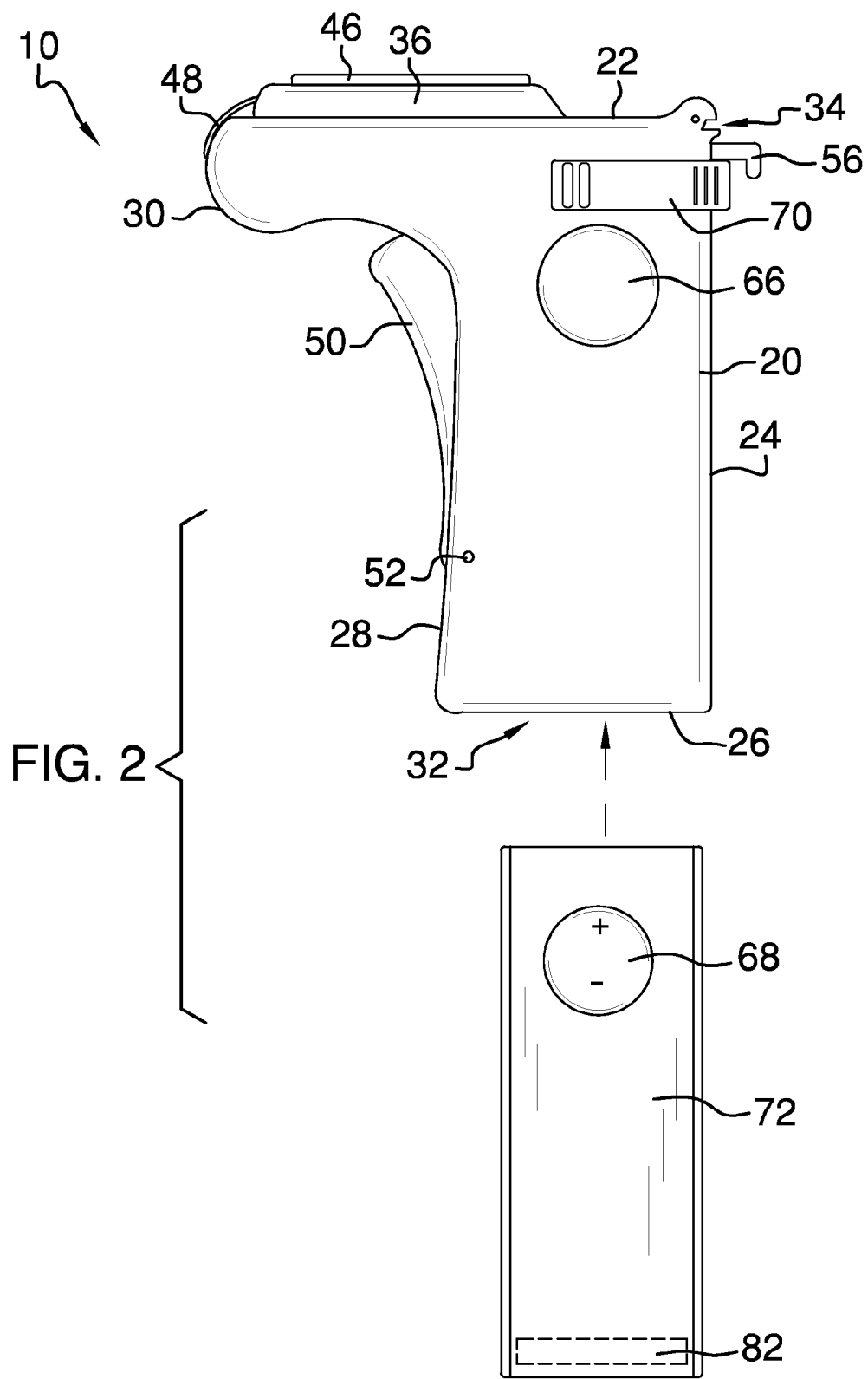
FIG. 2 is a side view with a cartridge removed from the device.
Figure 3:
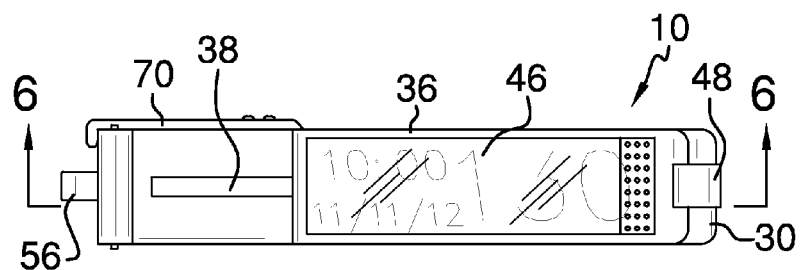
FIG. 3 is a top view.
Figure 4:
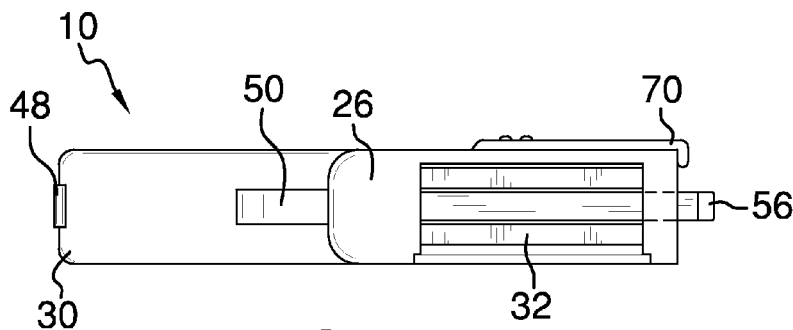
FIG. 4 is a bottom view.
Figure 5:
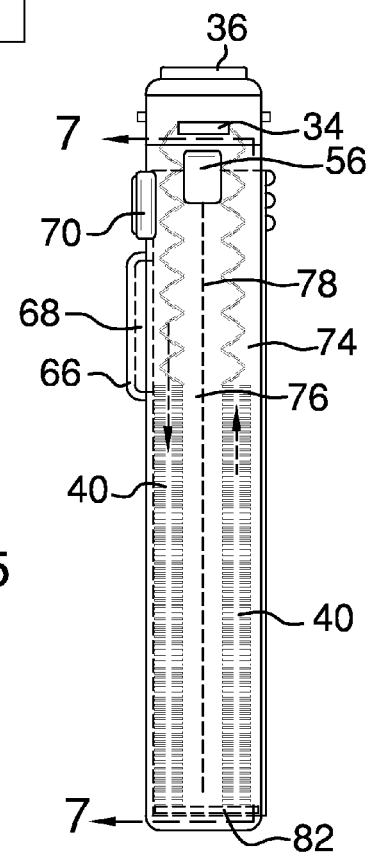
FIG. 5 is a front view with partial cutaway.
Figure 6:
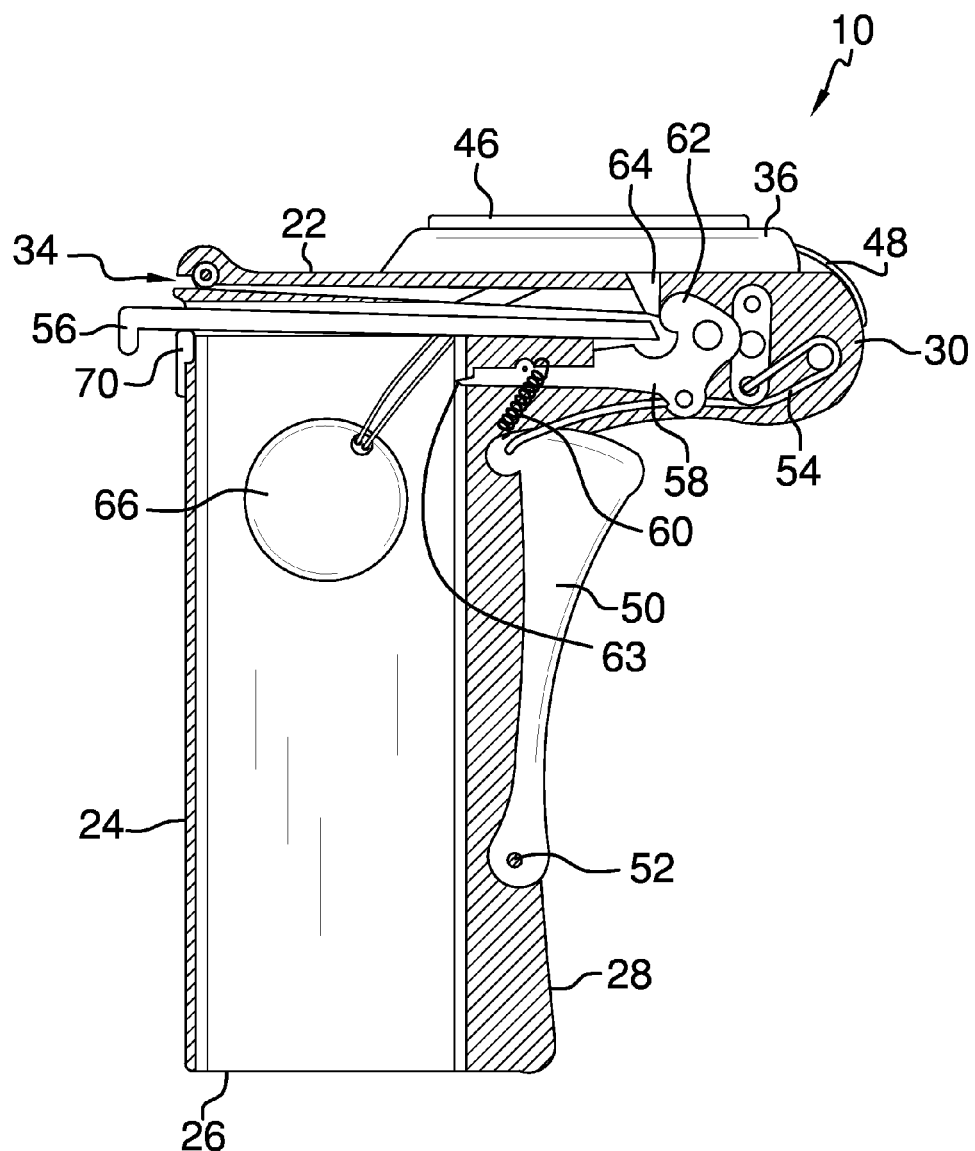
FIG. 6 is a cross-section view taken along the line 6-6 of FIG. 3.
Figure 7:
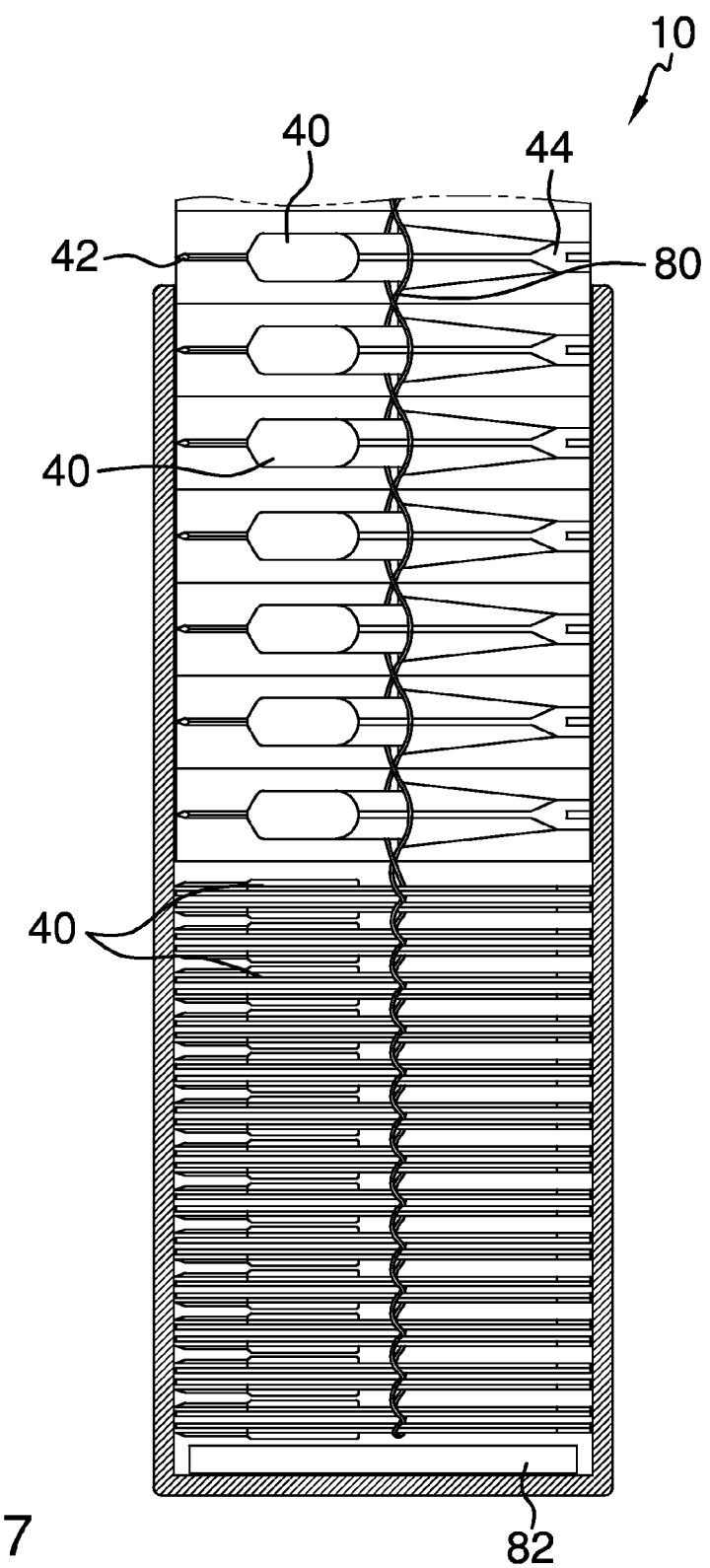
FIG. 7 is a cross-section view taken along the line 7-7 of FIG. 5.

With reference now to the drawings, and in particular FIGS. 1 through 7 thereof, example of the instant glucose blood monitor employing the principles and concepts of the present glucose blood monitor and generally designated by the reference number 10 will be described.

Referring to FIGS. 1 through 7 a preferred embodiment of the present glucose blood monitor 10 is illustrated.

The present glucose blood monitor 10 has been devised to enable one-handed use by a user monitoring glucose levels in the blood. The device 10 is configured to fit into one hand ergonomically. The device 10 is then placed against a section of epidermis wherein a cocking pin 56 is depressed to cock the device 10 for use and the thenar of the user's hand subsequently deploys a trigger mechanism 50 to fire the device 10. Upon firing, a hollow needle 42 of a lancet strip 40 is forced through a muzzle opening 34 into the user's epidermis to draw a sample of blood. The blood is drawn through the hollow needle 42 onto a test strip 44 which is engaged with a meter display assembly 36 concurrent with the action of firing the device 10. The meter display assembly 36 analyzes the blood sample and displays a glucose concentration upon a digital read out 46 disposed upon the meter display assembly 36.

Importantly, the present glucose blood monitor 10 employs the use of a cartridge 72 slidingly insertable into an interior cavity 32 disposed within the housing 20. A plurality of lancet strips 40 is disposed within the cartridge 72, each of said plurality of lancet strips 40 including a hollow needle 42 and a test strip 44. Each of the plurality of lancet strips 40 is disposed vertically one atop the other within a first cavity 74 disposed within the cartridge 72. An elastic coil 80 is disposed within the cartridge 72, said coil 80 encircling around each of the plurality of lancet strips 40. The elastic coil 80 repositions a lancet strip 40 subsequent firing, retaining the lancet strip 40 in a prime position, as will be detailed subsequently.

The glucose blood monitor 10, therefore, includes a housing 20 configured to slidingly receive and releasably secure a cartridge 72 within in an interior cavity 32. The housing 20 includes a top side 22, a front side 24, a bottom side 26, a rear side 28, an occipital bulb 30, and the interior cavity 32. The interior cavity 32 is accessible through the bottom side 26. A muzzle opening 34 is disposed upon the front side 24 proximal to the top side 22.

A meter display assembly 36 is slidably mounted to the top side 22 of the housing 20 proximal the occipital bulb 30. The meter display assembly 36 is mounted within a slot 38 enabling movement of the meter display assembly 36 between an unfired position proximal the occipital bulb 30 and a fired position, proximal the front side 24 of the housing 20. The meter display assembly 36 engages with a lancet strip 40 when said strip 40 is moved to a prime position by the act of cocking the device 10, as will be described subsequently. When the device 10 is fired, the meter display assembly 36 is accelerated towards the fired position and forcibly projects the lancet strip 40 forward.

When the meter display assembly 36 forcibly engages with said lancet strip 40 upon firing, two results occur. Firstly, the hollow needle 42 of the lancet strip 40 in question is forcibly projected out the muzzle opening 34 disposed on the device 10, whereupon the needle 42 pierces the epidermis of a user, and secondly, a test strip 44 is engaged with the meter display assembly 36 by the movement of the meter display assembly 36 subsequent the act of firing the device 10.

Blood drawn through the hollow needle 42 is registered upon the test strip 44 and analyzed by the meter display assembly 36 whereupon a glucose concentration is displayable upon the digital readout 46 disposed atop the meter display assembly 36. The meter display assembly 36 is returned to the unfired position by means of an elastic band 48 disposed upon the housing 20 over the occipital bulb 30.

To fire the device 10, a trigger mechanism 50 is disposed on the rear side 28 of the housing 20, said trigger mechanism 50 configured to be deployable with the thenar of a user's hand when the device 10 is grasped. The trigger mechanism 50 is hingedly attached to a swivel pin 52 disposed proximal the bottom side 26. The trigger mechanism 50 is therefore pivotable about the swivel pin 52 and moveable between a depressed position and a non-depressed position. When moved to the depressed position, the trigger mechanism 50 engages the release of a hammer mechanism 58 to fire the device 10, as will be described subsequently. A first spring member 54 is configured in operational communication with the trigger mechanism 50, said first spring member 54 forcibly returning the trigger mechanism 50 to the non-depressed position after depression and release of the trigger mechanism 50. The first spring member 54 has one end disposed on the trigger mechanism 50 and an opposite end attached to the hammer mechanism 58 within the occipital bulb. Thus, the trigger mechanism 50 is returned to the non-depressed position subsequent firing of the device 10 in order that a second firing may occur.

To cock the device 10 and ready the device 10 for firing, a depressible cocking pin 56 is disposed protruding out the front side 24 proximal to the muzzle opening 34. The cocking pin 56 is depressed when a user places the device 10 proximal the epidermis. The epidermis depresses the cocking pin 56, and the cocking pin 56 engages a hammer mechanism 58 within the housing 20, readying the device for firing upon depression of the trigger mechanism 50.

The hammer mechanism 58 is included within the housing 20 in operational communication with the trigger mechanism 50 and the cocking pin 56. The hammer mechanism 58 is moveable between a first position and a second position, said hammer mechanism 58 moved to the first position against the action of a coiled second spring member 60 when the cocking pin 56 is depressed and the device 10 is cocked. The hammer mechanism 58 is forced by means of the coiled second spring member 60 to the second position when the trigger mechanism 50 is deployed and the device 10 is fired.

The hammer mechanism 58 includes a convex rounded hammer member 62 configured to be contacted and moveably engaged by the cocking pin 56 when the device 10 is cocked, said rounded hammer member 62 configured to forcibly engage a concave foot member 64 disposed upon the meter display assembly 36 when the device 10 is fired, whereby the meter display assembly 36 is forcibly accelerated and a lancet strip 40 is moved thereby, wherein the hollow needle 42 is forced through the muzzle opening 34 and the test strip 44 is disposed within the meter display assembly 36.

The hammer mechanism 58 also includes a pointed end 63 disposed to contact a lancet strip 40 when the device 10 is cocked, whereby said lancet strip 40 is moved up into a prime position ready for firing, as will be described subsequently. The pointed end 63 therefore pivots upwards when the hammer mechanism 58 is moved to the second position and the device 10 is cocked, said pointed end 63 engaging against a lancet strip 40 to elevate said lancet strip 40 into the prime position for firing. A previously fired lancet strip 40 is displaced by the elevated lancet strip 40 when the device is cocked, as will be described subsequently.

A battery compartment 66 is disposed within the interior cavity 32, said battery compartment 66 configured to slidingly receive a button cell 68 therein. The battery compartment 66 is wired in circuit with the meter display assembly 36 to power the digital readout 46 and the analytic functioning of the meter display assembly 36 that analyzes the blood sample drawn by the device 10. The button cell 68 is disposed on the side of each cartridge 72 usable with the device 10 such that the act of loading the cartridge 72 positions the button cell 68 within the battery compartment 66. The button cell 68 is therefore changed with each cartridge 72, as desired.

To adjust the proximity of the muzzle opening 34 relative the epidermis of the user, a depth gauge 70 is moveably disposed proximal the cocking pin 56. The depth gauge 70 is moveable between a plurality of settings whereby the depth gauge 70 is positional to contact the skin of a user and delimit the proximity of the muzzle opening 34 thereby to the skin of the user. When the depth gauge 70 is extended to a minimum depth position, then the muzzle opening 34 of the device 10 is maintained at a least proximity to the epidermis of a user. When the depth gauge 70 is extended to a maximum depth position, then the muzzle opening 34 of the device 10 is maintained at a maximum proximity to the epidermis of a user, whereby firing the device 10 injects the hollow needle 42 to a greater depth within the epidermis.

The cartridge 72 is configured to releasably engage slidably into the interior cavity 32 through the bottom side 26 of the housing 20. The cartridge 72 includes a first cavity 74, a second cavity 76, and an interior wall 78 vertically dividing the first cavity 74 from the second cavity 76. The plurality of lancet strips 40 is disposed within the cartridge 72, each of said plurality of lancet strips 40 disposed vertically atop one another within the first cavity 74. Each of said lancet strips 40 includes a hollow needle 42, and a test strip 44. An elastic coil 80, disposed within the cartridge 72, is disposed around each of the lancet strips 40 to elastically return each lancet strip 40 to a prime position subsequent firing.

Each of the plurality of lancet strips 40 is cycled through the cartridge 72, from the first cavity 74 prior to use, and into the second cavity 76 subsequent use. During use, one of the plurality of lancet strips 40 is deployed from the cartridge 72 into a prime position when the cocking pin 56 is depressed and the device 10 is cocked. This lancet strip 40 is engaged by the meter display assembly 36 when the device 10 is fired, whereby the hollow needle 42 is projected through the muzzle opening 34 when the device 10 is fired, against the action of the elastic coil 80. The test strip 44 is loaded into the meter display assembly 36 into a read position by the motion of the meter display assembly 36, wherein blood drawn through the needle 42 is registered on the test strip 44 and read by the meter display assembly 36 and displayed upon the digital readout 46.

The hollow needle 42 is retracted from the muzzle opening 34 subsequent the action of firing the device 10 by means of the elastic coil 80 retractably forcing the lancet strip 40 back to the prime position. The lancet strip 40 is thereafter moved to a used position within the second cavity 76 when the device 10 is cocked a subsequent time and a subsequent lancet strip 40 is moved to the prime position from the first cavity 74. In this manner, each of the plurality of lancet strips 40 is moved from the first cavity 74 to the second cavity 76. When the last of the lancet strips 40 is moved to the second cavity 76, an absence of a subsequent lancet strip 40 is registered by the meter display assembly 36 to inform the user the cartridge 72 is expired. The cartridge 72 is then simply ejected from the device 10 for disposal, and a new cartridge 72 loaded for use.

A desiccating silica sac 82 is also included within the cartridge 72 to control moisture and lessen the potential for microbial growth therein.

What is claimed is:

1. A glucose blood monitor device comprising:
    a housing comprising:
        a top side;
        a front side;
        a bottom side;
        a rear side;
        an occipital bulb;
        an interior cavity accessible through the bottom side;
    a trigger mechanism disposed on the rear side, said trigger mechanism deployable with the thenar of a user's hand when the device is grasped;
    a muzzle opening disposed upon the front side proximal to the top side;
    a depressible cocking pin disposed protruding out the front side proximal to the muzzle opening;
    a hammer mechanism disposed within the housing, said hammer mechanism moveable between a first position and a second position whereby said hammer mechanism is moved to the first position against the action of a coiled second spring member when the device is cocked by depressing the cocking pin, and said hammer mechanism is forced by means of the coiled second spring member to the second position when the device is fired by deploying the trigger mechanism;
    a meter display assembly slidably mounted to the top side, said meter display assembly moveably engaged by the hammer mechanism;
    a cartridge configured to releasably engage slidably into the interior cavity through the bottom side, said cartridge comprising:
        a first cavity;
        a second cavity;
        an interior wall vertically dividing the first cavity from the second cavity;
        a plurality of lancet strips, each of said plurality of lancet strips disposed vertically atop one another within the first cavity, each of said lancet strips comprising:
            a hollow needle;
            a test strip; and
            an elastic coil disposed around each of the lancet strips;
        wherein one of the plurality of lancet strips is deployed from the cartridge into a prime position when the device is cocked by depressing the cocking pin, said lancet strip engaged by the meter display assembly when the device is fired, whereby the hollow needle is projected through the muzzle opening and the test strip is disposed within the meter display assembly when the device is fired against the action of the elastic coil, wherein blood drawn through the needle is registered on the test strip and read by the meter display assembly; and
        wherein the hollow needle is retracted from the muzzle opening subsequent the action of firing the device by means of the elastic coil retractably forcing the lancet strip back to the prime position, whereby said lancet strip is moved to the second cavity when the device is cocked a subsequent time.

2. The glucose blood monitor of claim 1 wherein the housing further comprises a battery compartment configured to house a button cell battery wired in circuit with the meter display assembly, said button cell battery disposed on the cartridge and loadable into the battery compartment when the cartridge is inserted into the interior cavity of the housing through the housing bottom end.

3. The glucose blood monitor of claim 2 wherein each of the plurality of lancet strips successively engages the meter display assembly;
    wherein the meter display assembly is configured to detect and notify the user when a last one of the lancet strips disposed within the cartridge is passed to the second cavity subsequent use.

4. The glucose blood monitor of claim 3 wherein the housing further comprises a depth gauge moveably disposed proximal to the cocking pin wherein the depth gauge is moveable between a plurality of settings whereby the depth gauge is positional to contact the skin of a user and delimit the proximity of the muzzle opening thereby to the skin of the user.

5. The glucose blood monitor of claim 4 wherein the trigger mechanism is rotatably hinged within the housing rear side by means of a swivel pin disposed proximal to the bottom opening, wherein the trigger mechanism is moveable between a depressed position and a non-depressed position, said trigger mechanism returned to the non-depressed position when released by a user by means of the action of a first spring member configured in operational communication with the trigger mechanism, the first spring member having one end disposed on the trigger mechanism and an opposite end attached to the hammer mechanism within the occipital bulb.

6. The glucose blood monitor of claim 5 wherein the hammer mechanism comprises:
    a convex rounded hammer member configured to be contacted and moveably engaged by the cocking pin when the device is cocked, said convex rounded hammer member configured to forcibly engage the meter display assembly when the device is fired, whereby the meter display member is forcibly accelerated and a lancet strip is moved thereby, wherein the hollow needle is forced through the muzzle opening and the test strip is disposed within the meter display assembly.

7. The glucose blood monitor of claim 6 wherein the meter display assembly further comprises a concave foot member, wherein the convex rounded hammer member accelerates the meter display assembly when the convex rounded hammer member engages the foot member.

8. The glucose blood monitor of claim 7 wherein the meter display assembly is moveable between a fired position more proximate to the front side of the housing than an unfired position, wherein the meter display assembly cycles each of the plurality of lancet strips between the prime position into a read position, wherein blood delivered to the test strip is readable by means of the meter display assembly, thence from the read position to a used position, whereby each of the plurality of lancet strips moves upwards within the first cavity and downwards within the second cavity.

9. The glucose blood monitor of claim 8 wherein the meter display assembly moves a lancet strip from the prime position into the read position when fired, said lancet strip subsequently moved to the used position when the device is cocked a subsequent time, whereby a next lancet strip is moved into the prime position concurrently when the device is cocked.

10. The glucose blood monitor of claim 9 wherein the cartridge further comprises a desiccating silica sac whereby moisture within the cartridge is controlled.

11. A glucose blood monitor device comprising:
   a housing comprising:
      a top side;
      a front side;
      a bottom side;
      a rear side;
      an occipital bulb;
      an interior cavity accessible through the bottom side;
      a battery compartment within the interior cavity, said battery compartment configured to slidingly receive a button cell therein;
   a trigger mechanism disposed on the rear side, said trigger mechanism configured to be deployable with the thenar of a user's hand when the device is grasped, said trigger mechanism comprising:
      a swivel pin disposed proximal to the bottom opening, the trigger mechanism pivotable about the swivel pin wherein the trigger mechanism is moveable between a depressed position and a non-depressed position;
      a first spring member configured in operational communication with the trigger mechanism, said first spring member forcibly returning the trigger mechanism to the non-depressed position;
   a muzzle opening disposed upon the front side proximal to the top side;
   a depressible cocking pin disposed protruding out the front side proximal to the muzzle opening;
   a meter display assembly slidably mounted to the top side, said meter display assembly comprising:
      a foot member disposed interiorly within the housing;
      a digital readout disposed atop the meter display assembly; wherein the meter display assembly is wired in circuit with the battery compartment;
   a hammer mechanism disposed within the housing, said hammer mechanism moveable between a first position and a second position, said hammer mechanism moved to the first position against the action of a coiled second spring member when the device is cocked by depressing the cocking pin, said hammer mechanism forced by means of the coiled second spring member to the second position when the device is fired by deploying the trigger mechanism, said hammer mechanism comprising:
      a rounded hammer member configured to be contacted and moveably engaged by the cocking pin when the device is cocked, said rounded hammer member configured to forcibly engage the foot member disposed upon the meter display assembly when the device is fired, whereby the meter display member is forcibly accelerated;
      wherein the first spring member has one end disposed on the trigger mechanism and an opposite end attached to the hammer mechanism within the occipital bulb;
   a depth gauge moveably disposed proximal to the cocking pin wherein the depth gauge is moveable between a plurality of settings whereby the depth gauge is positional to contact the skin of a user and delimit the proximity of the muzzle opening thereby to the skin of the user;
   a cartridge configured to releasably engage slidably into the interior cavity through the bottom side, said cartridge comprising:
      a first cavity;
      a second cavity;
      an interior wall vertically dividing the first cavity from the second cavity;
      a plurality of lancet strips, each of said plurality of lancet strips disposed vertically atop one another within the first cavity, each of said lancet strips comprising:
         a hollow needle;
         a test strip;
         an elastic coil disposed around each of the lancet strips;
      a button cell battery disposed on the cartridge, said button cell configured to load into the battery compartment when the cartridge is inserted into the interior cavity of the housing through the housing bottom end; and
      a desiccating silica sac whereby moisture within the cartridge is controlled;
   wherein one of the plurality of lancet strips is deployed from the cartridge into a prime position when the device is cocked by depressing the cocking pin, said lancet strip engaged by the meter display assembly in a read position within the meter display assembly when the device is fired, whereby the hollow needle is projected through the muzzle opening and the test strip is disposed within the meter display assembly when the device is fired against the action of the elastic coil, wherein blood drawn through the needle is registered on the test strip and read by the meter display assembly and a blood glucose level is displayed by the digital readout; and
   wherein the hollow needle is retracted from the muzzle opening subsequent the action of firing the device by means of the elastic coil retractably forcing the lancet strip back to the prime position, whereby the lancet strip is moved to the second cavity when the device is cocked a subsequent time.

12. The glucose blood monitor of claim 11 wherein the meter display assembly is moveable between a fired position more proximate to the front side of the housing than an unfired position, wherein the meter display assembly cycles each of the plurality of lancet strips between the prime position into a read position, wherein blood delivered to the test strip is readable by means of the meter display assembly, thence from the read position to a used position when the device is fired, whereby each of the plurality of lancet strips moves upwards within the first cavity and downwards within the second cavity.

13. The glucose blood monitor of claim 11 wherein the meter display assembly moves a lancet strip from the prime position into the read position when fired, said lancet strip subsequently moved to a used position in which the lancet strip is disposed within the second cavity when the device is cocked a subsequent time, whereby a next lancet strip is moved into the prime position concurrently when the device is cocked.

* * * * *